United States Patent [19]

Hinton et al.

[11] 3,977,203

[45] Aug. 31, 1976

[54] PURIFICATION OF NATURAL GAS BY LIQUID/LIQUID EXTRACTION WITH A POLAR SOLVENT

[75] Inventors: Robert A. Hinton, Mount Vernon, Ind.; Fred Kurata, Lawrence, Kans.

[73] Assignee: Kansas University Endowment Association, Lawrence, Kans.; by said Fred Kurata

[22] Filed: Mar. 25, 1974

[21] Appl. No.: 454,740

[52] U.S. Cl. .................................. 62/17; 55/56; 62/48; 208/240; 208/291; 208/311; 62/40; 62/20; 62/28
[51] Int. Cl.² ............................................... F25J 3/02
[58] Field of Search ............... 62/17, 20, 48; 55/56; 203/42, 43–46, 56, 63; 208/204, 232, 240, 291, 311, 332, 333

[56] References Cited
UNITED STATES PATENTS

| | | | |
|---|---|---|---|
| 2,863,527 | 12/1958 | Herbert et al. | 62/17 |
| 3,417,572 | 12/1968 | Pryor | 62/17 |
| 3,475,329 | 10/1969 | Little et al. | 62/17 |
| 3,657,375 | 4/1972 | Brunner et al. | 62/17 |
| 3,664,091 | 5/1972 | Hegwer | 62/17 |
| 3,718,006 | 2/1973 | Ranke et al. | 62/17 |
| 3,899,312 | 8/1975 | Kruis et al. | 62/17 |

*Primary Examiner*—Frank W. Lutter
*Assistant Examiner*—Frank Sever

[57] ABSTRACT

A gaseous stream (such as a "sour" natural gas stream) composed chiefly of a normally gaseous light hydrocarbon or alkane, such as methane, ethane, propane, or mixtures thereof, containing undesirable constituents, impurities or contaminants, such as carbon dioxide, hydrogen sulfide, water vapor, nitrogen and helium, is mixed with a polar organic liquid, such as methanol, or an aqueous solution of said liquid, such as an aqueous solution of methanol. The resulting mixture is cooled and liquefied and the resulting two-phase liquid mixture (comprising a light phase rich in the desired light hydrocarbon and an impurities-rich heavy phase of said polar organic liquid) is extracted with said polar organic liquid to recover said light hydrocarbon in the liquefied state, e.g. as liquefied, "sweet" natural gas.

11 Claims, 4 Drawing Figures

PURIFICATION OF NATURAL GAS BY LIQUID/LIQUID EXTRACTION WITH A POLAR SOLVENT

This invention relates to a low temperature process for the purification of a gaseous stream composed chiefly of normally gaseous lower alkanes, such as methane, ethane, and propane, and mixtures thereof, to remove undesirable constituents, impurities, or contaminants therefrom, and the recovery of the resulting purified stream in the liquefied state. In another aspect, this invention relates to a low temperature process for the purification of sour natural gas, and similar gaseous streams composed chiefly of methane, to remove undesirable constituents or impurities therefrom such as acidic gases, e.g., carbon dioxide and hydrogen sulfide, and water vapor, and the recovery of the purified natural gas in the liquefied state.

Natural gas, as produced from oil or gas wells or after processing to remove substantially all of the condensible propane and heavier hydrocarbons, comprises chiefly methane but contains significant amounts of undesirable constituents or impurities such as acidic gases, viz., carbon dioxide and/or hydrogen sulfide, nitrogen, helium, water vapor, and some light hydrocarbons, e.g., ethane and propane. A variety of processes have been disclosed or used for the removal of these constituents (e.g., see U.S. Pat. Nos. 3,393,527, 3,362,133, 3,339,342, 3,331,189, 3,255,572, 3,301,372, and 2,863,527). The present invention provides improved means for gas purification which affords significant processing, quality, and economic advantages in many applications.

Briefly, in a broad aspect of this invention, a natural gas stream containing undesirable constituents or impurities, such as carbon dioxide, is mixed with a normally liquid, inert, polar organic compound, such as methanol, or an aqueous solution thereof, such as aqueous methanol, said organic compound having a relatively low freezing point, e.g. below −80°C., and being sparingly miscible with liquefied methane. The resulting mixture is cooled and the bulk of the cooled mixture (except for non-condensed, inert gases that may be present therein, such as helium and nitrogen) is liquefied to form a twophase liquid mixture, the lighter phase comprising predominantly liquefied natural gas and the heavier liquid phase comprising predominantly said organic compound with absorbed impurities, e.g. carbon dioxide. The said twophase mixture is extracted at very low temperatures with a lean liquid stream of said polar organic compound in a liquid-liquid extraction zone without formation of a solid phase, and purified, liquefied natural gas is removed from said zone. The heavier liquid phase comprising predominantly said polar organic compound rich in constituents or impurities, e.g. carbon dioxide, desirably absorbed from the natural gas and some undesirably absorbed methane, can be stripped and lean polar organic compound recycled to the process.

Figure 4:
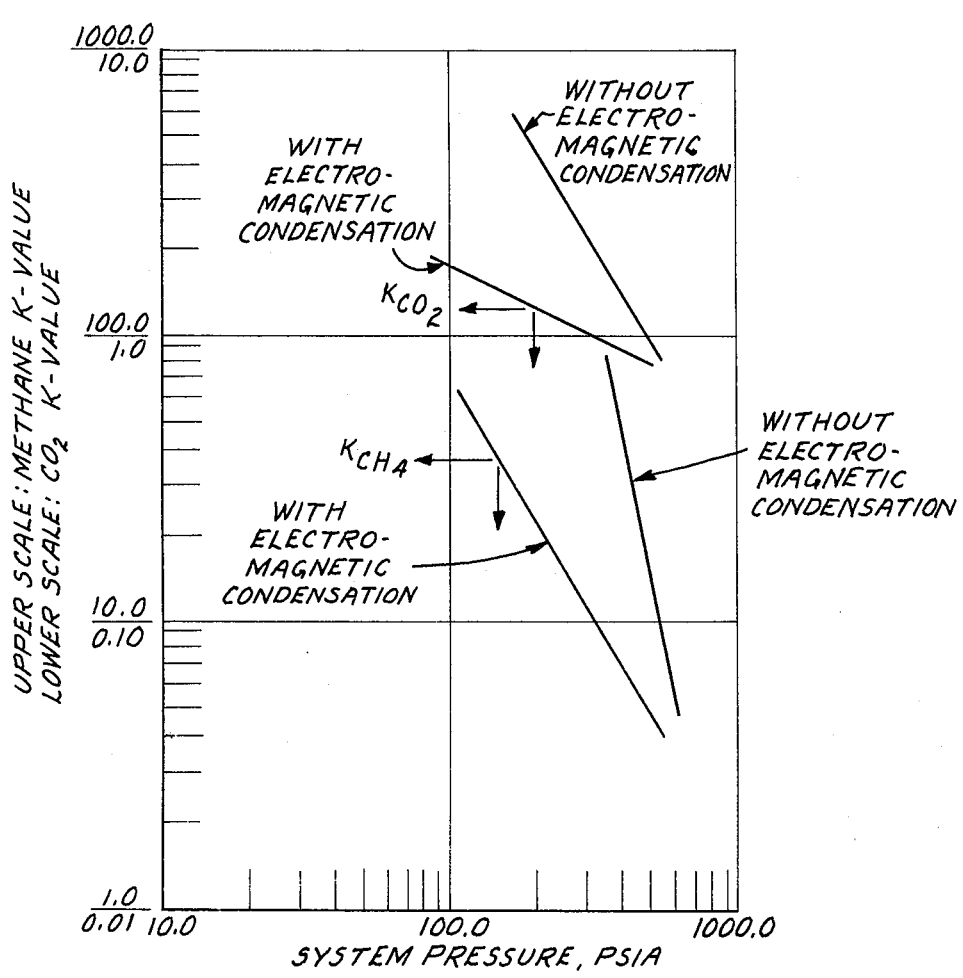

And FIG. 4 is a logarithmic plot of K values for methane and carbon dioxide in 40 mole % water in methanol at −75°C, illustrating the duplicity of volatilities for methane and carbon dioxide.

Figure 2:
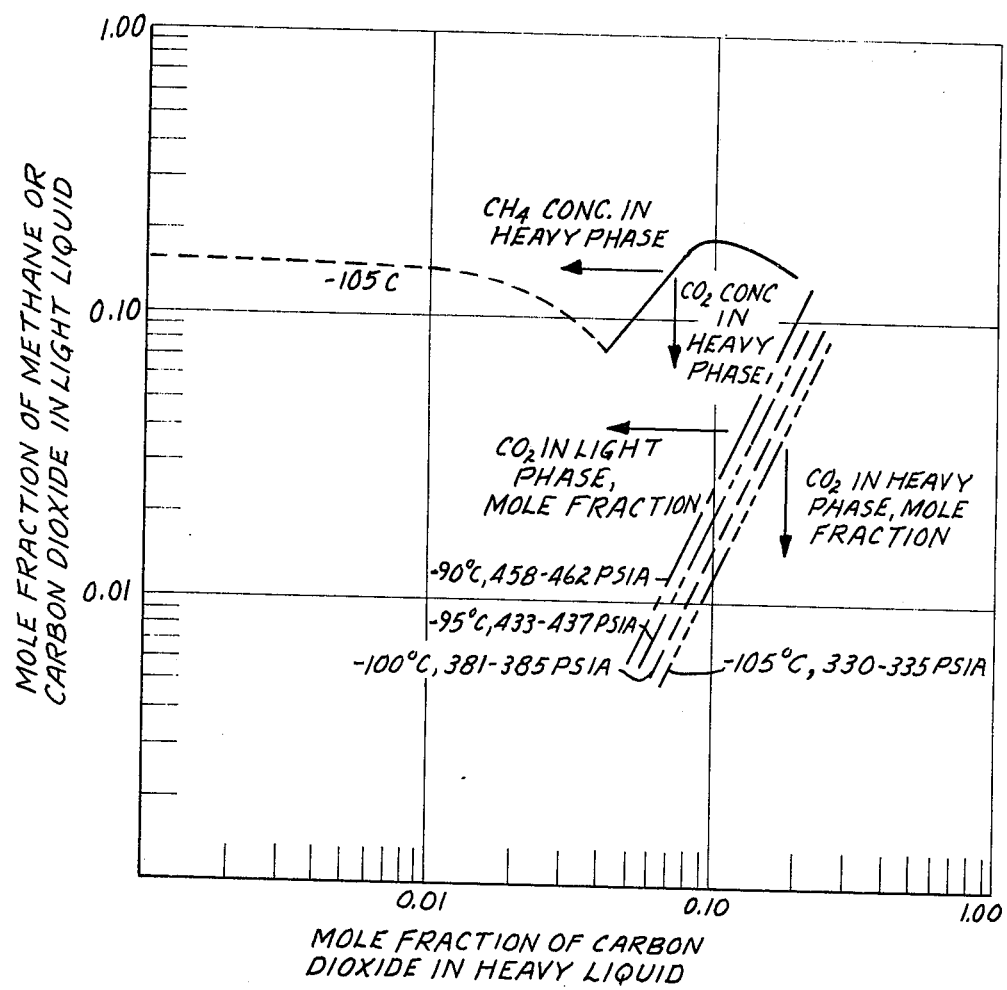
FIG. 2 is a logarithmic plot of liquid-liquid equilibria data for a three phase region of carbon dioxide-methane-methanol.
Figure 3:
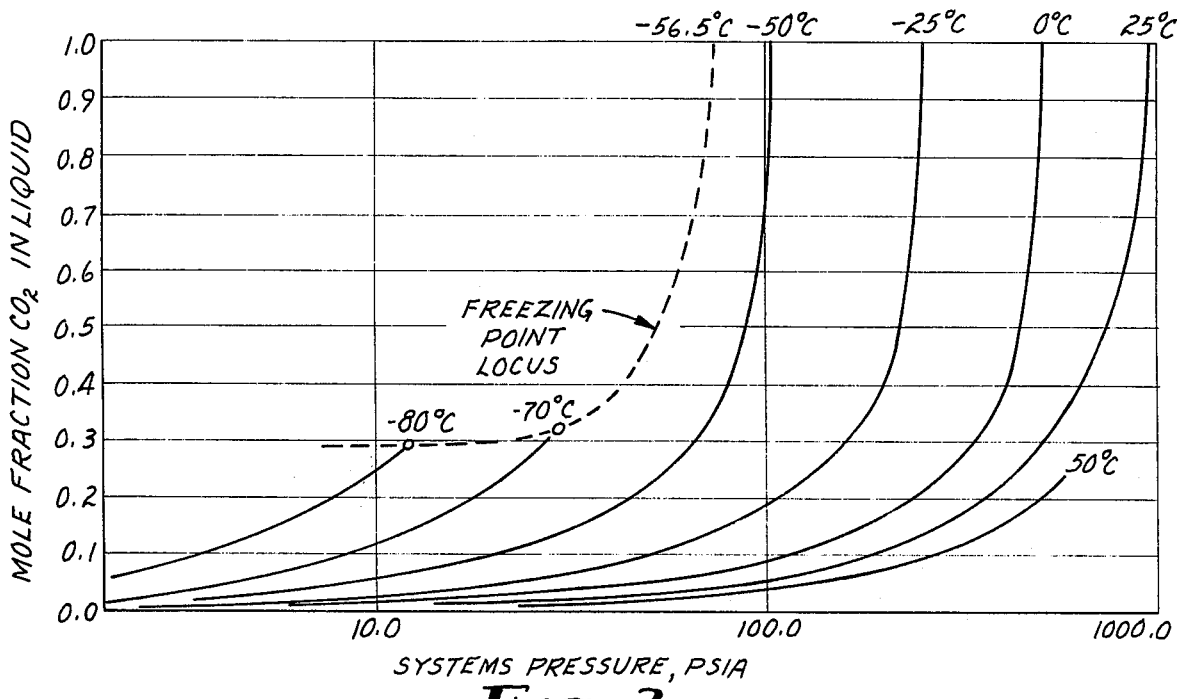
FIG. 3 is a logarithmic plot of the solubility of carbon dioxide in a methanol-water mixture containing 10 mole % water (i.e. a mole ratio of methanol:water of 9:1)

The data used in plotting FIGS. 2, 3, and 4 were obtained by the experimental procedure described in the article AIChE Journal, March 1971, pages 357–364. In this procedure, methanol or methanol-water mixture was admitted into the glass equilibrium cell; then methane gas and carbon dioxide were admitted into the cell at a predetermined pressure and this pressure was maintained by further injection of these gases while the temperature was lowered to the desired level by controlling the bath temperature. Since the cell and bath are made from glass, the presence of liquid phases or a solid phase can be visually observed. Samples of the various phases were withdrawn through the hypodermic tubing for analysis.

We have discovered that the polar organic compound exhibits unexpected behavior when mixed with contaminated natural gas at low temperature. In the case where methanol is the polar organic compound, this behavior is manifested as follows:

a. Methanol exhibits very limited miscibility with liquified methane;

b. Methanol will dissolve as much as 25 mole percent carbon dioxide at a temperature as low as −110°C without encountering a solid phase (more than 50°C below the normal freezing point of pure carbon dioxide);

c. Methanol will dissolve as much as 20 mole percent water at temperatures as low as −110°C without formation of a solid phase;

d. Above the temperature at which a solid phase appears, an increasing concentration of water increases the value of $\alpha$ (M/CD), the ratio of the methane (M) to carbon dioxide (CD) distribution coefficients (concentration in light phase/concentration in heavy phase) between the two liquid phases; although the distribution coefficients for both carbon dioxide and methane increase as the water concentration increases, the value for methane increases at a greater rate than the value for carbon dioxide; and e. The solubility of methane in the heavy liquid phase increases as the carbon dioxide concentration therein increases up to a maximum; above the maximum methane solubility of about 20 mole percent at about 10 mole percent carbon dioxide, the methane concentration begins to diminish with increasing carbon dioxide concentration (apparently the carbon dioxide displaces the methane in the liquid phase).

The phenomena mentioned in paragraphs a, b, and e above are illustrated in FIG. 2. FIG. 2 is a graphical presentation of the equilibrium compositions of the coexisting liquid phases for the ternary system of carbon dioxide-methane-methanol under conditions at which a vapor-light liquid-heavy liquid 3-phase system may exist at equilibrium. the equilibrium data are shown via two distinct sets of curves using common axis scales for both the ordinate and the abscissa. The upper discontinous curve with both a maximum and a minimum shows the relationship between the concentration of carbon dioxide in the heavy liquid phase and the solubility (concentration) of the methane in the same heavy liquid phase. The data show that the solubility of methane in this phase is about 16 mole % at a temperature of about −105°C when no cabon dioxide is present. This value is read at the left hand intercept of the broken line. The solubility of the methane in this heavy methanol rich liquid phase decreases to a "eutectic type" minimum of about 7.5 mole percent as the carbon dioxide concentration increases to about 4 mole percent. Thus the methanol concentration at this point is 88.5 mole percent and provides a methanol/carbon dioxide mole ratio of 22 for the minimum methane solubility. Above the 4 mole percent carbon dioxide concentration, the methane concentration increases to a maximum of 20 mole percent as the carbon dioxide concentration increases to 10 mole percent. Thus, the maximum methane solubility in the heavy liquid phase occurs at a methanol/carbon dioxide mole ratio of 7. The methane solubility in the heavy liquid phase decreases as the carbon dioxide concentration increases above 10 mole percent. For example, the methane solubility is only 15 mole percent at a carbon dioxide concentration of 20 mole percent. Hence, the methanol concentration is 65 mole percent at this point, providing a methanol/carbon dioxide mole ratio of 3.25. It is noteworthy that the solubility of methane in the heavy liquid phase is relatively independent of the temperature at methanol/carbon mole ratios of less than 22, i.e. at carbon dioxide concentrations greater than the "eutectic". Within the accuracy of the experimental equipment, a single curve described satisfactorily the methane and carbon dioxide concentrations in the heavy liquid phase at temperatures of −90°C, −95°C, −100°C, and −105°C for carbon dioxide concentration greater than 4 mole percent. The series of straight lines at −90°C, −95°C, −100°C, and −105°C gives the equilibrium distribution of carbon dioxide between the heavy liquid phase (methanol rich-abscissa) and the light liquid phase (methane rich-ordinate). These data show that lower temperatures gave a higher distribution of carbon dioxide in the methanol-rich, heavy liquid phase.

FIG. 3 is a graph which presents the solubility of carbon dioxide in a liquid phase comprising a solution of methanol and water with a mole ratio of 9:1 (10 mole % water on a carbon dioxide-free basis). The data are presented with the mole fraction carbon dioxide along the ordinate and the system pressure along the abscissa. Isotherms are utilized as parameters to present equilibrium data at −80, −70, −50, −25, 0, 25, and 50°C. The system freezing point locus is presented as a broken line.

Though this invention should not be bound to any theory, it appears that the above results are based upon unexpected thermodynamic phenomena which were observed by us experimentally. It is theorized that the polar organic liquid (e.g. methanol) exhibits adequate polarity of the electromagnetic field to induce a significant polarity into the normally symmetrical electromagnetic field of the methane molecule. An electromagnetic condensation occurs between methane, the polar organic compound, and polar impurities. As a consequence of the electromagnetic condensation phenomenon, a distinct thermodynamic species (or complex) may be formed. The complex exhibits an unexpectedly low solubility in the methane rich liquid phase, an unexpectedly high solubility of polar impurities in the polar organic compound, and an unexpectedly low freezing temperature of the polar organic liquid phase.

FIG. 4 illustrates the above theory of electromagnetic condensation via a mechanism of induced polarity. The K values (mole fraction in the vapor phase divided by mole fraction in the liquid phase) are presented along the ordinate as a function of pressure along the abscissa. Because of the great difference in the K values for methane and carbon dioxide, a dual-scale is utilized for the ordinate. The larger numbers (upper scale) are for methane and the smaller numbers (lower scale) are for carbon dioxide. The data illustrate that both methane and carbon dioxide may exhibit two distinct relationships between the K values and pressure at a constant temperature. We believe that the two distinct relationships correspond with systems either with or without electromagnetic condensation.

Explaining the unexpected phase behavior in other terms, the polar organic compound, such as methanol, may be cooled adequately to promote electromagnetic condensation with the impurities to form a distinct thermodynamic species. We theorize that the electromagnetic condensation occurs at reduced temperatures which are occasioned by a significant decrease in rotational energy levels. The permanent dipole moment (electromagnetic polarity) of the polar organic molecule is adequate to induce polarity into the electromagnetic field of the normally symmetric methane molecule. The molecules assume specific orientation of the positive to negative poles, and rotate as a distinct species in the liquid phase. This phenomena is manifested by the multiplicity of relative volatilities and distribution coefficients which were detected for the carbon dioxide and methane under conditions of constant temperature, pressure, and composition.

Figure 1:
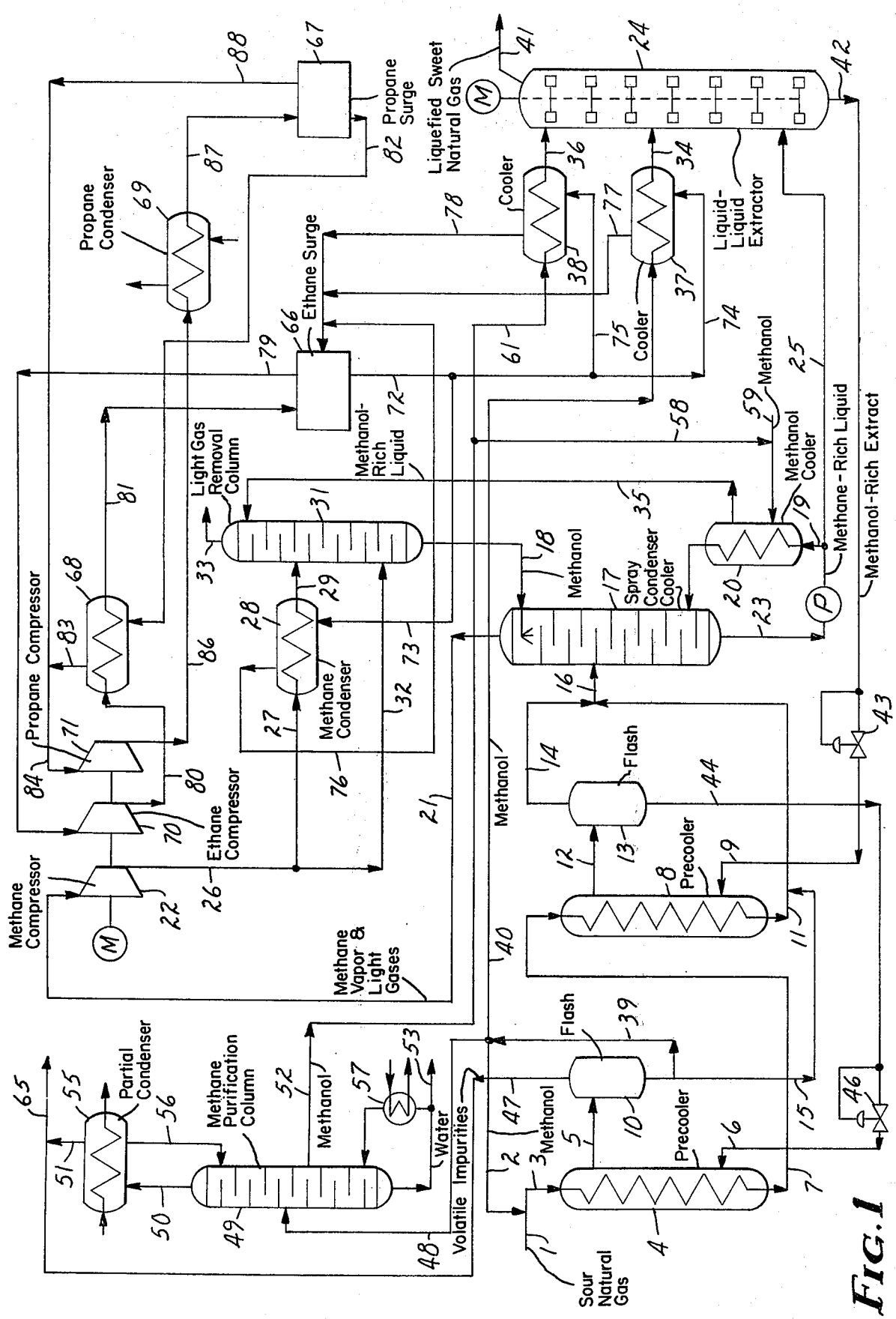
FIG. 1 is a schematic flowsheet illustrating a preferred embodiment of this invention.

In FIG. 1 of the accompanying drawing, a schematic flowsheet sets forth for illustrative purposes a preferred embodiment of this invention where a "sour" natural gas stream is processed to produce a purified or "sweet" liquefied natural gas product. As will be apparent, FIG. 1 sets forth for the purposes of illustration the principal pieces of equipment useful in said embodiment; valves, pumps, and other appurtenances which one skilled in the art will understand to be used have been omitted in the interest of brevity.

Natural gas (feedstock processed by this invention) is composed chiefly (e.g., at least 50 to 85 volume percent) of methane and contains significant amounts of other constituents whose presence is undesirable because they are impurities, e.g. carbon dioxide, hydrogen sulfide, and water vapor, or because such constituents, e.g. helium, are more valuable per se when removed from the natural gas. The natural gas stream processed by this invention will be delivered as feedstock to the process at 350–800 psia and 0°–200°F. A "sour" natural gas stream typical of those which are processed herein has the following compositions:

Table I

| Constituent | Amount, vol. % |
|---|---|
| Methane | 75 |
| Ethane | 8 |
| Propane | 3 |
| Heavier hydrocarbons | 4 |
| Carbon dioxide | 5 |
| Hydrogen sulfide | 2.5 |
| Nitrogen | 2 |
| Helium | 0.1 |
| Water vapor | 0.4 |
| | 100.0 |

As a preliminary to the liquefaction of the natural gas process stream, the natural gas feedstock stream (designated by reference number 1 in FIG. 1) is precooled to conserve the process energy requirements of said liquefaction (heat exchangers for this purpose are denoted in FIG. 1 as precoolers 4 and 8). Since the feedstock will normally contain water vapor, carbon dioxide, and other constituents which will freeze or form solid hydrates and foul heat transfer surface used in said precooling operation, the feedstock is first mixed with a stream comprising a normally liquid, low molecular weight, polar organic compound (occasionally referred to herein as a solvent) which has a normal freezing point below −80°C., a strong dipole moment (greater than or equal to that of acetone), is inert (i.e. chemically non-reactive) with respect to the natural gas constituents, and exhibits limited miscibility with liquefied methane. A sufficient amount of the polar organic compound is mixed with the feedstock so that the polar compound prevents the formation of ice and solids such as hydrates. Examples of such polar organic compounds are methanol, ethanol, n-propanol, isopropanol, acetone, and the like. Where the preferred polar compound, methanol, is used, the amount thereof mixed with the feedstock is that sufficient to provide about 2 to 4 moles of methanol per mole of impurities in the feedstock to prevent formation of a solid phase. In another aspect of this invention, the polar organic compound is mixed with water to form an aqueous solution, such as aqueous methanol, containing sufficient amount of said polar organic compound.

After precooling the gaseous admixture of feedstock and polar organic compound, e.g., to a temperature between the freezing point of water (0°C) and the freezing point of carbon dioxide (−56°C), the precooled gaseous admixture is further cooled to effect complete liquefaction thereof — with exception of inert, non-condensible gases, e.g., helium and nitrogen, which are more volatile than methane. This liquefaction is preferably carried out in a spray condenser-stripper (designated by reference number 17 in FIG. 1) equipped with several liquid-vapor contacting stages to promote contacting between the entering precooled gaseous process stream and an adequate amount of a liquid stream comprising said polar organic compound sprayed onto the top contacting stage to absorb major fractions of acidic impurities such as carbon dioxide and hydrogen sulfide. The condenser-stripper provides stripping mass transfer stages to eliminate from the resultant liquefied product (subsequently conveyed via lines 23, 25 to the extractor 24) those compounds more volatile than methane, such as nitrogen and helium. The resultant mixture of the two immiscible liquid phases (the light phase being methane rich and the heavy phase being methanol rich) is withdrawn from the bottom of spray-condenser-stripper unit and a portion of the liquid mixture vaporized, e.g., in a thermosiphon reboiler, and returned to the unit to strip helium and light gases, such as nitrogen and helium, from the methane rich phase, the resultant stripped gases and vaporized methane being removed (via line 21) from the top of the column, as overhead. The condenser-stripper provides sufficient rectifying mass transfer stages to prevent corrosive impurities, such as water vapor, carbon dioxide and hydrogen sulfide, from entering the overhead and having a deleterious effect in the compressor and condenser units which process the overhead stream.

The spray-condenser-stripper unit can operate at temperatures from about −100°F to about −170°F, which corresponds to a pressure range from about 650 to 300 psia, depending upon the concentration of heavier hydrocarbons (i.e., ethane and higher alkanes) in the system. The preferred conditions for the unit are −135°F and 400 psia at the bottom with the top operated near the boiling point of pure methane, i.e., about −145°F at 400 psia.

The two-phase liquid mixture in effluent stream 25 is passed to an extraction unit, which is preferably a multi-stage liquid-liquid extraction column (designated by reference number 24 in the drawing), where it is purified or extracted with said liquid polar organic compound. The number of contacting stages, e.g., trays, can be determined on the basis of purification requirements for each specific process installation. Primary variables which will affect the number of actual contacting stages include: (a) the concentration of impurities in the sour natural gas feedstock; (b) the physical and chemical properties of the polar organic compound; (c) the extractor operating temperature; (d) the maximum concentration of impurities specified or permitted in the purified or "sweet" natural gas product; (e) and the economical balance of costs for either additional extractor stages or increased rate of circulation of the polar organic compound through the extractor. With these variables in mind and the equilibrium data for the distribution of impurities between the two liquid phases in the extractor (the relatively heavy phase rich in polar organic compound and the relatively light methane rich phase), the calculation of the number of separation stages requied for a specified, liquid natural gas product can be performed by those skilled in the art.

Where the extractor is a multi-stage, liquid-liquid extraction column (the preferred extraction unit), the liquefied natural gas stream is purified by countercurrent contact with the liquid polar organic compound, the liquefied natural gas stream passing up through the extractor to the top settling stage. The resultant purified, liquid, methane-rich natural gas is withdrawn from the top of the extractor as product (designated by line 41 in the drawing) and the polar organic compound with extracted, absorbed impurities is withdrawn from the bottom settling stage of the extractor. The extract can be stripped of the absorbed impurities, for example by flashing (the preferred stripping operation), multistage counter-current stripping, extractive distillation, etc., and the resulting lean polar organic compound recycled to the extractor.

The liquid-liquid extraction operation is carried out at temperatures (e.g., −80° to −120°F) below the freezing point of the impurities in the liquefied natural gas and, surprisingly, this operation can be carried out without formation of solid phases of the impurities, e.g., ice or hydrate. Also, the operation can be carried out without the foaming and entrainment problems often encountered with vapor-liquid contacting processes. The greater density of the liquefied natural gas that is extracted in the liquid-liquid operation of this invention permits a capital investment (for the extractor) which is lower as compared with a vapor-liquid purification unit. And the low temperatures used in the liquid-liquid extraction permits operation at pressures lower than commonly employed for vapor-liquid contacting, the extractor requiring pressures which need be only sufficient above the pressure of the spray-condenser-stripper to prevent formation of a vapor phase in the extractor. The extractor operates adiabatically with the exception of heat leak through the insulation and heat input by an mechanical means of agitating the two liquids introduced into the extractor. The preferred operating conditions for the extractor are an isothermal temperature profile with pressure at least 20 psia greater than that of the spray-condenser-stripper.

The polar organic compounds useful as extraction solvents are those described above. Here, too, in the liquid-liquid extraction step, methanol is the preferred polar organic compound to be used, since we have discovered that it can extract as much as 25 weight percent carbon dioxide from a carbon dioxide-methane mixture at temperatures as low as −165° F. without encountering a solid phase (this temperature being more than 80° F. below the freezing point of pure carbon dioxide). And we further prefer to use aqueous methanol as the extraction solvent, since we have discovered that even with the methanol-solvent mixture containing substantial amounts of water (e.g., 20 mole percent), the extraction can be carried out at temperatures well below the freezing point of carbon dioxide without encountering a solid phase and that with increasing concentration of water in the methanol-solvent stream the ratios of the distribution coefficients for methane and carbon dioxide is improved, i.e., the distribution coefficient (concentration in light phase/concentration in heavy phase) for both carbon dioxide and methane increases, with the value for methane increasing at a greater rate than the value for carbon dioxide. The maximum of the methane concentration in the heavy liquid phase or extract, with increasing concentration of carbon dioxide in that phase, is surprisingly low, carbon dioxide apparently displacing methane in that phase.

Referring to FIG. 1 of the accompanying drawing, sour natural gas feedstock (e.g. having the composition of Table I, supra) is delivered to the process by stream 1, this gas generally having a temperature between 0° and 200°F and a pressure of 350 to 800 psia, preferably 100°F and 450 psia. The feedstock 1 is admixed with a sufficient amount of a methanol-rich stream 2 to prevent water ice or hydrate from forming in the feedstock and fouling the heat transfer surface of the precoolers to which the resulting mixed stream 3 is subsequently conveyed. The amount of methanol used for this purpose will generally be 0.50 to 4.0 moles per mole of water in the resulting mixture, and preferably two moles of methanol per mole of water. In the first or primary precooler 4 (which unit can be a shell and tube heat exchanger with either vertical or horizontal orientation), heat or energy is removed from the mixed stream 3 on the tube side by heating and partial vaporization of heat exchange medium supplied via line 6 on the shell side of the precooler. There is removed from the precooler 4 a precooled process stream 7 having a decrease in enthalpy manifested in a decrease in temperature and partial condensation thereof, the amount of energy transferred depending upon the temperature, composition, and flow rate of the heat exchange medium 6 and the heat transfer area of the precooler 4. Generally, the temperature of the precooled stream 7 will be between −10° and +50°F, preferably about +20°F at 420 psia. The heat exchange medium, having an increase in its enthalpy, is removed from the upper end of precooler 4 via line 5 and passed to a vapor-liquid separation tank 10. Stream 7 is then passed to secondary precooler (similar in construction and operation to that of precooler 4) where the process stream is further precooled by indirect heat exchange with heat exchange medium 9, the resulting further precooled stream 11 having a further decrease in enthalpy, the amount of energy transferred being dependent upon the composition, temperature, and flow rate of heat exchange medium 9 and the amount of heat transfer surface in the secondary precooler 8. The further precooled stream 11 will generally have a temperataure between −40° and +20°F, preferably about −25°F at 400 psia. Heat exchange medium with an increase in enthalpy is removed via line 12 from the upper end of precooler 8 and passed to a vapor-liquid separation tank 13.

The precooled process stream 11 is admixed with methane-rich vapor product supplied via line 14 from separation tank 13 and can be further admixed with a methanol stream 15 supplied from the separation tank 10. The resulting mixed stream 16 is then introduced into the mid-section of a spray-condenser-stripper 17. In order to prevent impurities in the mixed stream 16 from freezing or forming a solid phase, the mixed stream generally should contain about 1.0 to 6.0 moles methanol per total mole impurities, preferably 4 moles methanol per total mole impurities, e.g. water. A condensed mixture of methane and methanol is supplied to the top of the condenser-stripper 17 via line 18 and a methane-rich gas stream is supplied via line 19 to the bottom of the condenser-stripper.

The condenser-stripper 17 and condenser 28 substantially liquefy the bulk of the condensible components in the feed 16 and to this end it will generally operate from about −110°F. to about −170° F. and 650 to 300 psia, depending upon the concentration of heavier hydrocarbons (i.e., ethane and higher alkanes) in the process stream, the preferred conditions at the bottom of the unit being about −135° F. and about 400 psia and the top of the unit operating near the boiling point of pure methane, i.e., about −145° F. at 400 psia. The liquefied product of the condenser-stripper 17 is withdrawn via line 23 as a two-phase mixture (comprising a methanol-rich, heavy phase containing absorbed high freezing point impurities and a methane-rich, light phase), and it is conveyed to the bottom mixing stage of liquid-liquid extractor 24.

Some methane, helium and other light gases such as nitrogen are removed as overhead via line 21 from the top of the condenser-stripper 17. The boil-up required to strip helium and other light gases in the packed or tray section of condenser-stripper 17 below the feed entry point is provided by recycling to the bottom sections of the condenser-stripper a portion of the liquefied product 23 via line 19 through methanol cooler 20. Methane vapor and light gases, 21, are passed into a methane compressor 22 at about −145° F. and 395 psia, and the resulting compressed stream is discharged therefrom via line 26 and passed via line 27 to methane condenser 28. The discharge pressure of stream 26 depends upon the characteristics of the refrigerant 73 supplied to the methane condenser 28, which in the case of the ethane refrigerant 73 will be about 580 psia, which provides a 15° F. temperature difference between the methane condensation at −125° F. and the ethane evaporation at −140° F. and 10 psia.

The condensed methane stream 29 is passed from methane condenser 28 into the mid-section of a light gas removal column 31 which functions as a stripperabsorber to remove (via overhead line 33) compounds, such as helium and nitrogen, which are more volatile than methane, and the overhead being of significant by-product value because of the substantial quantity of helium therein. Column 31 has absorption mass transfer stages above the feed entry point and strpping mass transfer stages below the feed entry point. A small amount of the methane compressor effluent 26 is introduced via line 32 into the bottom of the light gas removal column 31, this effluent serving to strip compounds more volatile than methane from the liquid feed stream 29. A methanol-rich stream from methanol cooler 20 is introduced via line 35 into the top of column 31 at about −125°F (this stream can be further precooled, e.g. down to about −170°F, if required for lower methane concentration in overhead stream 33). Methane and traces of less volatile compounds are absorbed into the methanol-rich liquid phase in the mass transfer stages above the feed entry point of the light gas removal column 31. A two-phase liquid stream (comprising a methane-rich light phase and a methanol rich heavy phase) is removed from the bottom of column 31 and passed via line 18 to the top of condenser-stripper 17 as described above. Column 31 operates essentially isothermally at the boiling point of pure methane, preferably about 580 psia and −125°F.

In addition to charging the two-phase stream 23 from condenser-stripper 17 to the liquid-liquid extractor 24, two methanol solvent streams are also charged to the latter, viz. stream 34 and stream 36 from precoolers 37 and 38, respectively. Stream 34, supplied to an intermediate mixing stage of the extractor 24, is the direct recycle stream supplied via lines 39, 40 from the bottom of separation tank 10. Though stream 34 contains low concentrations of impurities, it will dissolve a substantial quantity of impurities and provide a savings of operating costs as compared with utilization of purified methanol only. Stream 36 is a purified methanol stream, supplied to the top mixing stage of the extractor 24; this stream serving to extract residual impurities from the liquid methane-rich phase which are in equilibrium with the concentration of impurities in stream 34.

Extractor 24 is provided with a sufficient number of stages, the exact number being dependent upon the equilibrium for the distribution of impurities between the two liquid phases in the extractor (viz. the relatively heavy methanol-rich phase and the relatively light methane-rich phase). The range of operating conditions for the extractor 24 is essentially the same as that provided for the condenser-stripper 17, the preferred operating conditions being an isothermal temperature profile with pressure at least 20 psi greater than that in the condenser-stripper to prevent solid phase formation.

A purified, liquid methane-rich phase of "sweet" liquefied natural gas stream is withdrawn as product via line 41 from the top of the extractor 24, this product stream being conveniently transferred to liquid storage or containerized shipment. A heavy methanol-rich extract is withdrawn via lin 42 from the base of extractor 24 and passed to secondary precooler 8 and then to separation tank 13 (which functions as a vapor-liquid separation unit), the concentrations of impurities in the extract being dependent upon the relative flow rates of the extraction solvent in lines 34, 36 and the impurities in the feedstream 25. The molar ratio of methanol to impurities should be maintained above about 4 to 1 to avoid formation of a solid phase. The concentration of dissolved methane and higher alkanes in the extract stream 42 will be a function of the temperature and the concentrations of impurities. For example, as the concentration of carbon dioxide is increased from 5 mole percent to 10 mole percent at −157°F, the equilibrium concentration of methane is increased from 9.5 mole percent to 20 mole percent. As the carbon dioxide concentration is further increased to 17 mole percent, the equilibrium concentration of methane is diminished to about 16.5 mole percent. (These data are illustrated in FIG. 2.)

Provision of a controlled amount of water in the circulating methanol is advantageous for minimizing the solubility of alkanes in the extractor effluent stream 42. For example, maintenance of one mole of water for every four moles of methanol in the solvent phase diminishes the methane solubility to about 6.5 mole percent with 7.0 mole percent of carbon dioxide and to about 10 mole percent with 15.5 mole percent of carbon dioxide (temperature of −157°F). Thus, the provision of one mole of water for every four moles of methanol diminishes the methane solubility about 35 percent in the optimum range of impurity concentration. The lower methane concentration decreases the operating costs of methane recycle from the primary separation tank 13.

The extract stream 42 is expanded by expansion valve 43 and the expanded stream passed via line 9 to the bottom of secondary precooler 8 where partial vaporization is aided by indirect heat exchange with the precooled stream 7. The resulting stream with higher enthalpy and lower pressure is passed via line 12 to primary separation tank 13. The temperature and pressure of stream 12 can vary depending upon the relative flow rates and compositions of streams 7 and 9, the preferred conditions for the primary separation tank 13 being about −60°F and 150 psia.

Because of a higher relative volatility, an enriched methane gas will be discharged via line 14 from the primary separation tank 13. The total energy input into stream 9 is controlled to provide the degree of methane vaporization required, which preferably is about 80 percent vaporization of the methane contained in stream 9. The methane to carbon dioxide relative volatility for the flash operation will be about 12.0; the methane to hydrogen sulfide relative volatility will be about 50.0 (the relative volatility as used herein being the ratio of the K values, the K value being computed as the mole fraction of a constituent in the vapor phase divided by the mole fraction of the same constituent in the liquid phase). The methanol-rich solvent phase (containing the majority of impurities) is discharged via line 44 from the bottom of the primary flash tank 13 and expanded by expansion valve 46, the expanded stream being passed via line 6 to the primary precooler 4.

Partial vaporization of the stream 6 and an increase of its enthalpy results from indirect heat exchange with the process stream 3. The partially vaporized stream is passed via line 5 to the separation tank 10 (which functions as a secondary separation unit vis-a-vis separation tank 13), the temperature and degree of vaporization of stream 5 depending upon the composition, flow rates and enthalpy of streams 3 and 6. The secondary separation tank 10 is operated at sufficiently high pressure and sufficiently low temperature to vaporize at least 50 percent of the volatile impurities contained in stream 5, the preferred flash operating conditions being −13°F at 30 psia, at which conditions the solubility of carbon dioxide is about 4.0 mole percent in a solvent phase containing 4 moles of methanol per mole of water. The residual methane and low molecular weight alkanes will also be vaporized in the secondary separation tank 10.

The overhead, rich in impurities, from tank 10 is removed via line 47 and it can be purged from the process, re-injected into the soil via a disposal well, delivered to a sulfur recovery unit, or otherwise disposed of. The liquid stream removed from the bottom of the secondary separation tank 10 contains low concentrations of carbon dioxide and hydrogen sulfide; however, it is suitable for direct recycle to the following points in the process: via line 15 to condenser-stripper 17; via lines 39, 2 to feed stream 1; via lines 39, 40 to liquid-extractor 24; and via lines 39, 48 to methanol purification column 49.

The functions of the column 49 may be summarized as follows:

a. to eliminate via lines 50, 51 impurities more volatile than methanol as a gaseous produce from a section of rectifying mass transfer stages above the feed entry point;

b. to recover a recycle methanol solvent stream free of volatile impurities and denuded of heavy impurities via side-draw stream 52;

c. to eliminate impurities less volatile than methanol as a liquid product which is withdrawn via line 53 from the bottom of the column, this stream comprising predominantly water which is purged from the system.

Methanol purification column 49 is provided with a sufficient number of mass transfer stages, the particular number employed being dependent upon the feed composition, the desired composition of the product streams produced therefrom, and the vapor-liquid equilibrium. Column 49 can be operated at a pressure of about 25 psia, a bottom temperature of about 220°F, and an overhead product temperature of about 110°F (which is about the lowest temperature at which satisfactory reflux conditions can be sustained utilizing cooling tower water in the partial condenser 55). Higher pressure operation may be desired to minimize methanol loss in stream 51 (which contains hydrogen sulfide, carbon dioxide and residual light hydrocarbons). Stream 51 can be admixed with stream 47 and purged therewith via line 65 as discussed above.

Methanol solvent side-draw stream 52, free of volatile impurities and denuded of heavy impurities, can be recycled to the following process points: to methanol cooler 20 via line 58 for admixture with makeup methanol supplied via line 59; and via line 61 as extract charge to the top stage of liquid-liquid extractor 24.

A refrigeration system of the cascade type is shown in FIG. 1 for the purpose of refrigerating methane condenser 28 and methanol coolers 37, 38. The system comprises an ethane surge tank 66, propane surge tank 67, ethane condenser 68, propane condenser 69, and an ethane compressor 70 and propane compressor 71, these compressors being driven together with methane compressor 22 by a gas-fired turbine or the like. Condensed ethane is supplied from ethane surge tank 66 via lines 72, 73 to refrigerate methane condenser 28 and via lines 72, 74, 75 to refrigerate methanol coolers 37, 38, the refrigerant then being returned to the surge tank from the condenser 28 via line 76 and from coolers 37, 38 via lines 77, 78. Ethane vapor from surge tank 66 is passed via line 79 to ethane compressor 70, the compressed ethane passed via line 80 to ethane condenser 68, and the condensed ethane returned via line 81 to the surge tank. For purposes of refrigerating ethane condenser 68, propane refrigerant is passed from propane surge tank 67 via line 82 to condenser 68 where it vaporizes, propane vapor being passed via lines 83, 84 to propane compressor 71, the compressed propane being passed via line 86 to water-cooled propane condenser 69, and condensed propane being returned via line 87 to propane surge tank 67, propane vapor therefrom being passed via lines 88, 84 to propane compressor 71. The ethane and propane required for this refrigeration system can be obtained if desired by fractionation of the liquid gas product 41. Other refrigeration systems can be used, however, such as chlorinated and fluorinated hydrocarbons.

Various modifications and alterations of this invention will be apparent to those skilled in the art without departing from the scope and spirit of this invention. For example, the use of a portion of stream 18 in one or more stripping stages at the base of the extractor 24 (for the purpose of diminishing the concentration of ethane and higher molecular weight hydrocarbons in stream 42) is within the scope of the invention.

What is claimed is:

1. In a process for the purification of a gaseous stream comprising chiefly methane and small amounts of carbon dioxide, hydrogen sulfide, and water vapor as undesirable constituents wherein said gaseous stream is mixed with a liquid, inert polar organic compound, and cooled, the improvement comprising liquefying condensible components in the resulting mixture by subjecting the same to a temperature of −110°F to −170°F and a pressure of 650 to 300 psia to form a liquid mixture of two immiscible liquid phases, the lighter phase comprising a methane-rich phase and the heavier phase comprising a phase rich in said polar organic compound, and extracting the resulting liquefied product with said liquid polar organic compound in a liquid-liquid extraction zone to separate and recover a purified, liquefied stream of methane.

2. In a process for the purification of a sour natural gas stream containing methane, carbon dioxide, hydrogen sulfide, water, helium and nitrogen wherein said stream is mixed with methanol and the resulting mixture is cooled, the improvement comprising liquefying condensible components in said resulting mixture by subjecting the same to a temperature of −110°F to −170°F and a pressure of 650 to 300 psia to form a liquid mixture of two immiscible phases, the lighter phase comprising a methane-rich phase and the heavier phase comprising a methanol-rich phase, extracting the resulting liquefied product with methanol in a liquid-liquid extraction zone at temperatures below the freezing point of said carbon dioxide, and separating the resulting extract from the resulting purified, liquefied sweet natural gas product.

3. The process of claim 2, wherein said cooling step is carried out at a temperature between the freezing point of water and the freezing point of carbon dioxide.

4. The process of claim 3, wherein said cooling step is carried out at −40°F. to +20°F.

5. The process of claim 2, wherein said extracting step is carried out at −110°F. to −170°F.

6. The process of claim 2, wherein the amount of methanol mixed with said sour natural gas stream is sufficient to provide 1 to 25 moles methanol per mole of carbon dioxide and 0.5 to 25 moles methanol per mole water.

7. The process of claim 2, wherein the amount of methanol mixed with said liquefied product in said extracting step is 0.01 to 1.0 moles per mole of liquid methane.

8. The process of claim 2, wherein absorbed impurities are removed from said extract and the resulting recovered methanol is recycled to said process.

9. The process of claim 2, wherein said methanol mixed with said natural gas stream and used to extract said liquefied product is aqueous methanol.

10. The process of claim 2, wherein said methanol mixed with said natural gas stream and used to extract said liquefied product is a mixture of methanol and another polar solvent such as another alcohol, a ketone, or ketone and water.

11. In a process for the purification of a gaseous stream comprising chiefly methane and carbon dioxide, hydrogen sulfide and water vapor as undesirable constituents wherein said gaseous stream is contacted with liquid aqueous methanol precooled to a temperature between the freezing point of water and the freezing point of carbon dioxide, the improvement comprising liquefying condensible components in the resulting precooled mixture by subjecting the same to a temperature of $-110°F$ to $-170°F$ and a pressure of 650 to 350 psia to form a liquid mixture of two immiscible liquid phases, the lighter phase comprising a methane-rich phase and the heavier phase comprising a methanol-rich phase with said undesirable constituents absorbed therein, passing said liquid mixture to a liquid-liquid extraction zone and extracting therein said lighter phase with liquid aqueous methanol at temperatures below the freezing point of carbon dioxide to provide a heavy liquid methanol-rich phase containing undesirable constituents absorbed therein and a light liquid methane-rich phase, and recovering the latter phase as the purified product of the process.

* * * * *